US010801016B2

(12) United States Patent
Faust et al.

(10) Patent No.: US 10,801,016 B2
(45) Date of Patent: Oct. 13, 2020

(54) OPTICAL-QUALITY SURFACE THAT IMPARTS SPATIAL CONTROL OF MACROPHAGE FUSION

(71) Applicants: Arizona Board of Regents on Behalf of Arizona State University, Scottsdale, AZ (US); UNIVERSITY OF NOTRE DAME DU LAC, South Bend, IN (US)

(72) Inventors: James Faust, Tempe, AZ (US); Tatiana Ugarova, Phoenix, AZ (US); Robert Ros, Phoenix, AZ (US); Wayne Christenson, Mesa, AZ (US); Kyle Doudrick, South Bend, IN (US)

(73) Assignees: Arizona Board of Regents on Behalf of Arizona State University, Scottsdale, AZ (US); University of Notre Dame du Lac, South Bend, IN (US)

( * ) Notice: Subject to any disclaimer, the term of this patent is extended or adjusted under 35 U.S.C. 154(b) by 13 days.

(21) Appl. No.: 15/699,974

(22) Filed: Sep. 8, 2017

(65) Prior Publication Data
US 2018/0066234 A1    Mar. 8, 2018

Related U.S. Application Data

(60) Provisional application No. 62/385,141, filed on Sep. 8, 2016.

(51) Int. Cl.
G02B 21/34    (2006.01)
C12N 5/16    (2006.01)
(Continued)

(52) U.S. Cl.
CPC ............... *C12N 5/16* (2013.01); *C12M 23/20* (2013.01); *C12M 25/00* (2013.01); *C12N 5/0645* (2013.01); *G01N 33/5005* (2013.01); *G01N 33/5032* (2013.01); *G01N 33/5055* (2013.01); *G02B 21/34* (2013.01); *C12N 2533/12* (2013.01); *C12N 2533/20* (2013.01); (Continued)

(58) Field of Classification Search
None
See application file for complete search history.

(56) References Cited

U.S. PATENT DOCUMENTS

| 2,770,609 A | 11/1956 | Symonds | |
|---|---|---|---|
| 3,963,432 A * | 6/1976 | Hauxwell | A01N 25/30 8/609 |
| 2004/0018615 A1* | 1/2004 | Garyantes | B01F 13/0071 435/305.2 |

OTHER PUBLICATIONS

NPL document "FluoroDishTM Glass Bottom Petri Dishes", a webpage from http://www.tedpella.com/pdfs_html/FluoroDish-glass-bottom-dishes.pdf accessed on Oct. 23, 2019, online since Jun. 20, 2007 according to Google (see p. 1) (Year: 2007).*

(Continued)

*Primary Examiner* — Renee Claytor
*Assistant Examiner* — Trent R Clarke
(74) *Attorney, Agent, or Firm* — Quarles & Brady LLP; Jessica L. Lewis

(57) ABSTRACT

Methods to form a surface coating and surface pattern, which are based on adsorption of hydrocarbon chains that can be used with imaging optics to visualize macrophage fusion and multinucleated giant cell formation with living specimens are described.

15 Claims, 9 Drawing Sheets

(51) Int. Cl.
  C12N 5/0786 (2010.01)
  G01N 33/50 (2006.01)
  C12M 1/12 (2006.01)
  C12M 1/00 (2006.01)
(52) U.S. Cl.
  CPC ...... C12N 2535/00 (2013.01); C12N 2535/10 (2013.01); C12N 2537/00 (2013.01); C12N 2539/00 (2013.01)

(56) References Cited

OTHER PUBLICATIONS

James J. Faust, Wayne Christenson, Kyle Doudrick, Robert Ros, Tatiana P. Ugarova, Development of fusogenic glass surfaces that impart spatiotemporal control over macrophage fusion: Direct visualization of multinucleated giant cell formation, 2017, Biomaterials, vol. 128, pp. 160-171 (Year: 2017).*

NPL document "Cover Glass at Thomas Scientific" is a webpage at Thomas Scientific accessed at https://www.thomassci.com/scientific-supplies/Cover-Glass on Oct. 25, 2019, online since Dec. 6, 2013 according to Google (see p. 1). (Year: 2013).*

Terry O. Collier, Carson H. Thomas, James M. Anderson, Kevin E. Healy, Surface chemistry control of monocyte and macrophage adhesion, morphology, and fusion, 2000, J. Biomed. Mater. Res., vol. 49, No. 1, pp. 141-145 (Year: 2000).*

Anderson, J. et al., "Foreign body reaction to biomaterials", Seminars in Immunology, Apr. 2008 (epub Dec. 2007), 20(2), pp. 86-100.

Christenson, W. et al., "Combined single cell AFM manipulation and TIRFM for probing the molecular stability of multilayer fibrinogen matrices", Ultramicroscopy, Jan. 2014 (epub Oct. 2013), 136, pp. 211-215.

Helming, L. et la., "Molecular mediators of macrophage fusion", Trends in Cell Biology, Oct. 2009 (epub Sep. 2009), 19(10), pp. 514-522.

Helming, L. et la., "The molecular basis of macrophage fusion", Immunobiology, Jan. 2008 (epub Nov. 2007), 212(9-10), pp. 785-793.

Jenney, C. et al., "Human monocyte/macrophage adhesion, macrophage motility, and IL-4-induced foreign body giant cell formation on silane-modified surfaces in vitro", Student Research Award in the Master's Degree Candidate Category, 24th Annual Meeting of the Society for Biomaterials, San Diego, CA, Apr. 22-26, 1998, Journal of Biomedical Materials Research, 41(2), Aug. 1998, pp. 171-184.

Lishko, V. et al., "The interplay between integrins $\alpha m\beta 2$ and $\alpha 5\beta 1$ during cell migration to fibronectin", Experimental Cell Research, Feb. 2003 (epub 2003), 283(3), pp. 116-126.

McInnes, A. et al., "Interleukin 4 induces cultured monocytes/macrophages to form giant multinucleated cells", Journal of Experimental Medicine, Feb. 1988, 167(2), pp. 598-611.

McNally, A. et al., "Interleukin-4 induces foreign body giant cells from human monocytes/macrophages. Differential lymphokine regulation of macrophage fusion leads to morphological variants of multinucleated giant cells", American Journal of Pathology, Nov. 1995, 147(5), pp. 1487-1499.

Olivier, N. et al., "Simple buffers for 3D STORM microscopy", Biomedical Optiics Express, Jun. 2013 (epub May 2013), 4(6), pp. 885-899.

Riedl, J. et al., "Lifeact mice for studying F-actin dynamics", Nature Methods, Mar. 2010, 7(3), pp. 168-169.

Wolter, S. et al., "rapidSTORM: accurate, fast open-source software for localization microscopy", Nature Methods, Nov. 2012, 9(11), pp. 1040-1041.

Zhao, Q. et al., "Foreign-body giant cells and polyurethane biostability: in vivo correlation of cell adhesion and surface cracking", Journal of Bio,edical Materials Research, Feb. 1991, 25(2), pp. 177-183.

* cited by examiner

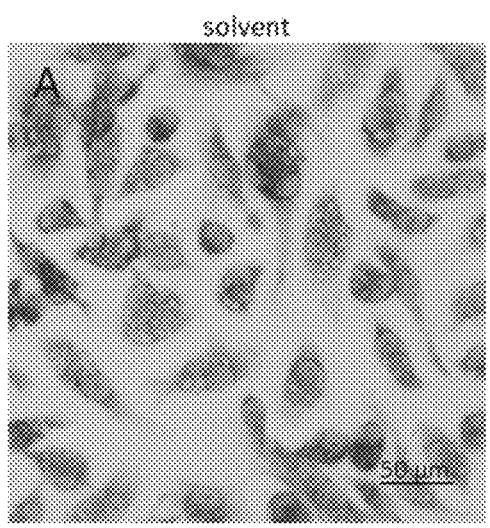
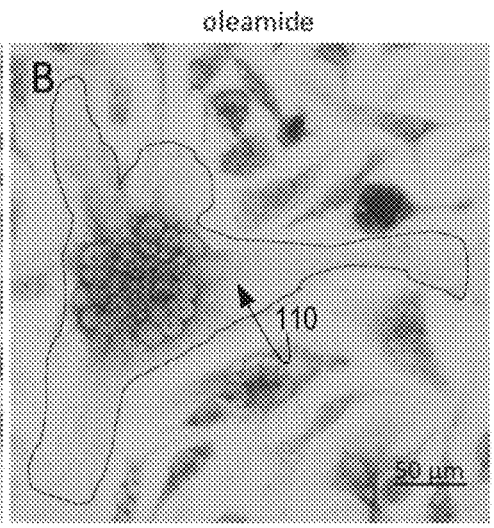
FIG. 1A  FIG. 1B
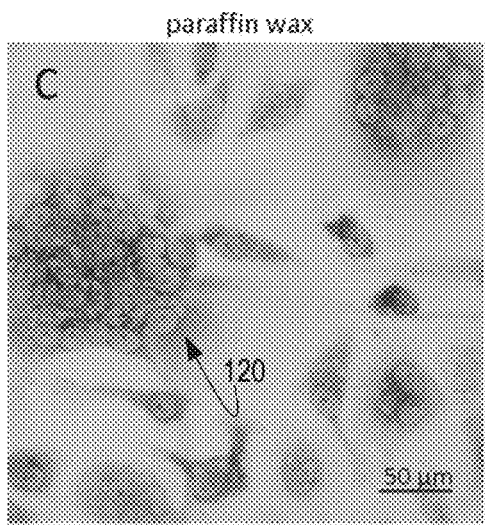
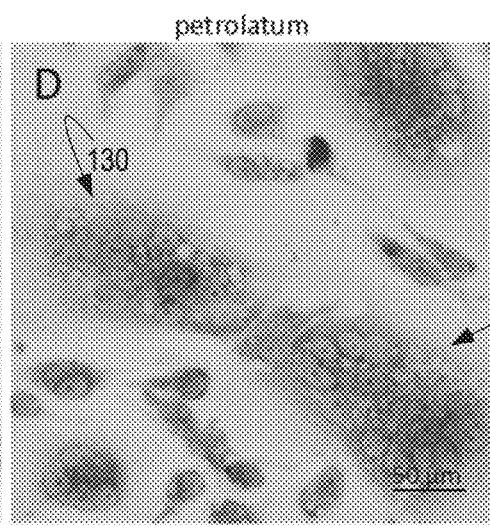
FIG. 1C  FIG. 1D

OPTICAL-QUALITY SURFACE THAT IMPARTS SPATIAL CONTROL OF MACROPHAGE FUSION

CROSS-REFERENCE TO RELATED APPLICATION

This application claims priority to U.S. Provisional Patent Application No. 62/385,141 filed on Sep. 8, 2016, the disclosure of which is incorporated herein by reference.

STATEMENT REGARDING FEDERALLY SPONSORED RESEARCH

This invention was made with government support under R01 HL63199 awarded by the National Institutes of Health. The government has certain rights in the invention.

FIELD OF INVENTION

This disclosure generally relates to apparatus and methods involving a surface coating and surface pattern based on deposition of hydrocarbon chains that can be used with imaging optics to visualize macrophage fusion and multinucleated giant cell formation in living specimens via a light microscope.

BACKGROUND

The formation of multinucleated giant cells, derived from fusion of mononucleated macrophages, occurs as a consequence of a number of pathological conditions in the body. In vitro visualization of macrophage fusion and the formation of multinucleated giant cells with living specimens to date has not been shown. This deficiency in the literature is due to the fact that no surface exists promoting macrophage fusion while maintaining optical properties necessary for advanced imaging techniques with a microscope.

SUMMARY

Applicant's disclosure describes the discovery of a surface coating that promotes high rates of macrophage fusion on a glass surface. Further, the surface includes micropatterns with different surface roughness. This surface coating is compatible with microscope techniques known in the art.

Embodiments of the present disclosure describe a method of adhering a monocyte or macrophage to a glass surface such that cell fusion occurs and can be visualized via light microscopy. The method further comprises a step of adsorbing the glass slide in a solution containing a hydrocarbon and the step of contacting said monocyte or macrophage to the surface under conditions suitable for cell fusion.

Further, other embodiments of the present disclosure describe an apparatus for visualizing cell fusion with a microscope. The apparatus comprises an optically clear glass surface having a hydrocarbon surface coating with a pattern and a glass slide.

In yet other embodiments, the present disclosure describes another method for visualizing macrophage fusion in living specimens with light microscopy. The method further comprises a step of contacting a monocyte or macrophage to hydrocarbon surface of an optically clear slide under conditions that induce cell fusion and a step of visualizing said cell fusion with said light microscopy.

BRIEF DESCRIPTION OF DRAWINGS

FIG. 1A shows that deposition of non-covalently coupled hydrocarbon chains promotes macrophage fusion on optical-quality glass. Deposition of solvent alone, as a control for the ability of dried solvent to promote fusion, results in low-levels of fusion.

FIG. 1B shows that deposition of oleamide results in high-levels of macrophage fusion. The dashed lines enclose a multinucleated cell.

FIG. 1C shows that deposition of DMSO-free paraffin results in high-levels of macrophage fusion.

FIG. 1D shows that deposition of tocopherol-free petrolatum results in high-levels of macrophage fusion. Fused macrophages are evidenced by 2 or more nuclei within the cell.

DETAILED DESCRIPTION

Figure 1E:
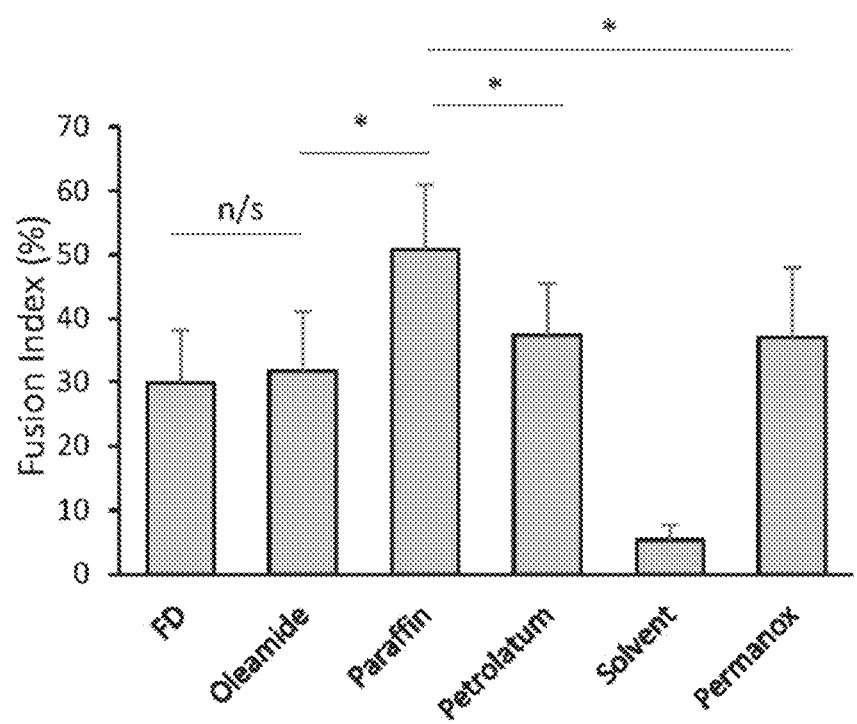
FIG. 1E shows quantification of fusion indexes for each surface. A fusion index on Permanox was determined under identical culture conditions. Results shown are means±S.D from three independent experiments each with three to five bright field images analyzed. *$p<0.05$ as determined by ANOVA. The scale bars in the lower right corner of each micrograph are 50 µm.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The present disclosure describes an optical-quality glass surface with a hydrocarbon coating with or without a micropattern, i.e., defined regions, and methods to form same that can impart spatial control of cell fusion while maintaining optical properties necessary for any microscope technique known in the art, specifically for advanced imaging techniques with the light microscope. Therefore, macrophage fusion and multinucleated giant cell formation in living specimens can be visualized in vitro and live imaged under a microscope.

As described herein, "about" is defined to mean a plus or minus 10% difference in any measurement. Multinucleated giant cells (MGCs) are defined by their formation, which entails upon triggering foreign body reaction, extravasation of monocytes, differentiation of monocytes into macrophages, and subsequent fusion of macrophages to form foreign body giant cells. The formation of MGCs results in increased production of potent cellular products designed to clear the foreign body.

In certain embodiments, a glass slide that is made of borosilicate glass can be utilized. The thickness of the borosilicate glass is dependent on the microscope objective but usually can range from about 0.10 mm to 0.25 mm. The preferred range of the thickness of the borosilicate glass is about 0.13 mm to 0.17 mm. The borosilicate glass possesses certain optical characteristics and hydrolytic consistency so that such glass is optically compatible with microscope techniques known in the art. In other embodiments, other types of surfaces that are optically clear, such as certain types of plastics can also be utilized.

The glass surface has a hydrocarbon coating that promotes cell fusion, particularly, the glass surface is able to promote high rates of macrophage fusion, i.e., about 59% of macrophages fuse after 24 hours in the presence of interleukin-4. In certain embodiments, the glass comprises a surface coating of organic compounds comprising hydrocarbons. In certain embodiments, hydrocarbons that have a solid physical state at a range of temperature of about 30° C. to about 40° C. can be used to adsorb the glass surface. In other embodiments, hydrocarbons that have a semi-solid physical state at a range of temperature of about 30° C. to about 40° C. can be used to adsorb the glass surface. Further, in yet other embodiments, the hydrocarbons are selected from a group consisting of one or more of an oleamide having a following structure 1, a paraffin wax having a following structure 2, and a petrolatum having a following structure 3.

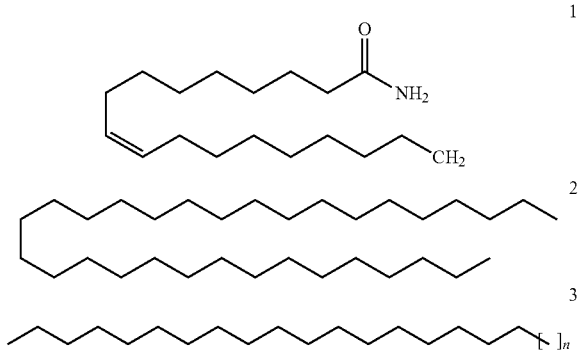

In certain embodiments, the glass surface with hydrocarbon adsorption comprises a surface roughness ($R_a$), which is expressed in nanometers and can be measured and characterized by atomic force microscopy (AFM). In certain embodiments, micropatterned glass surface increases in its $R_a$ and further increases in macrophage fusion rate with a higher degree of spatiotemporal control over the formation of MGCs.

Figure 4:
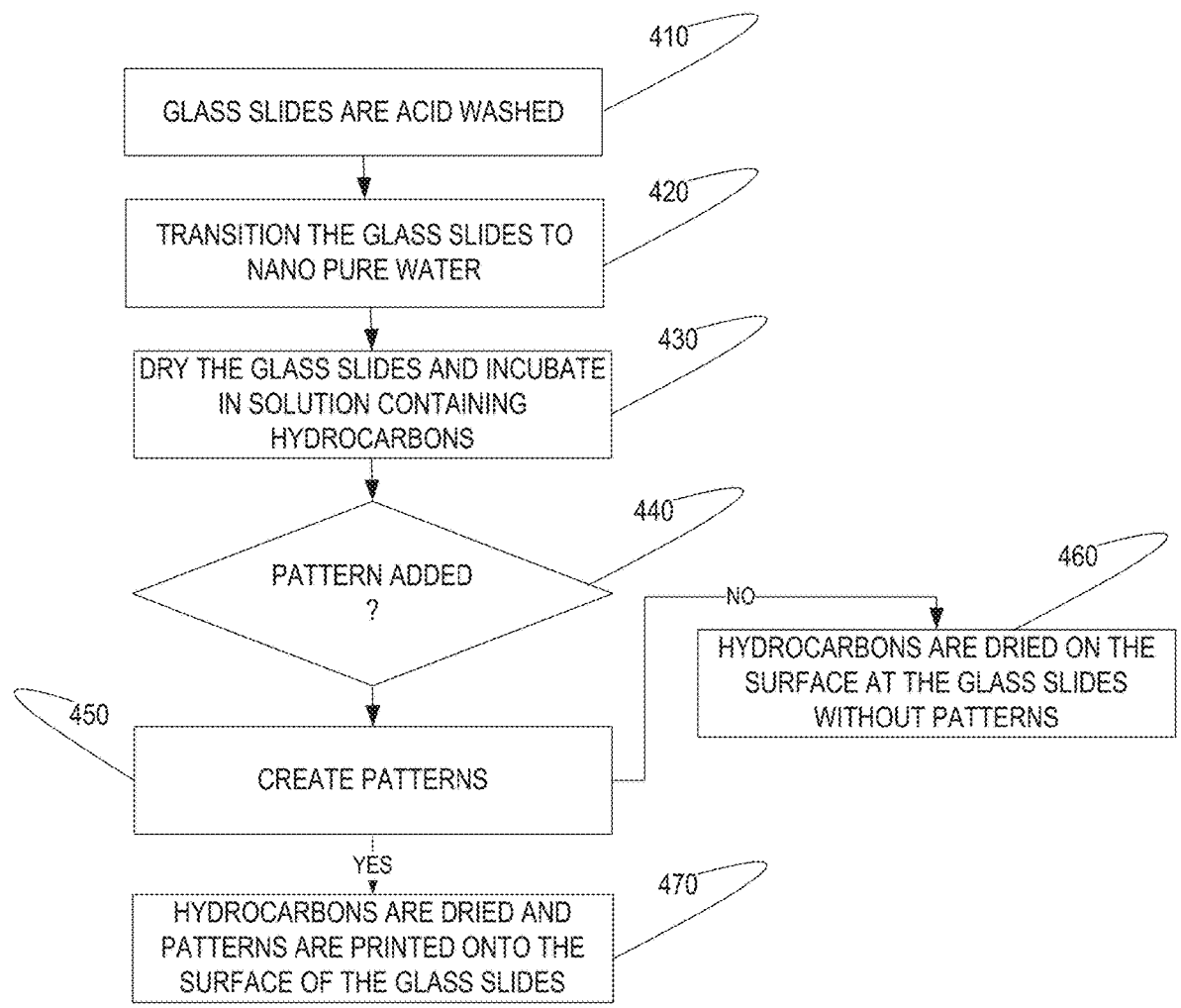
FIG. 4 is a flowchart summarizing the method to form a glass surface with a hydrocarbon coating with or without a micropattern.

Now referring to FIG. 4, a flowchart showing the method to make the glass slide with the surface able to promote high rates of cell fusion is illustrated. In step 410, borosilicate glass slides (0.13-0.17 mm; Deckglaser, Deutsche Spiegelglas) are acid washed in an acidic solution of about 6 M HCl for three times for 30 minutes each. Each time the HCl solution is changed. Other suitable acids that are known in the art can also be used to make the acidic solution.

In step 420, the borosilicate glass slides are transitioned to nanopure water, and subsequently stored in absolute ethanol until use. In step 430, in certain embodiments, immediately before use the borosilicate glass are dried and incubated for about 5 seconds in a solution of about 1 mg/ml paraffin wax (Sigma Aldrich, 327212) in spectrophotometry grade toluene to form a surface coating of hydrocarbons. In other embodiments, immediately before use the borosilicate glass are dried and incubated for about 5 seconds in a solution of about 1 mg/ml oleamide in spectrophotometry grade isopropanol to form a surface coating of hydrocarbons. In yet other embodiments, immediately before use the borosilicate glass are dried and incubated for about 5 seconds in a solution of about 10 mg/ml petrolatum in spectrophotometry grade toluene to form a surface coating of hydrocarbons.

In step 440, the method provides an option for imprinting a pattern to the surface of the glass slides. If a pattern is added, the method transitions to step 450. In step 450, in certain embodiments, micropattern stamps, such as a PDMS, are used to create surface patterns. In other embodiments, masks are fabricated according to standard procedures to create surface patterns.

If a pattern is not preferred, the method transitions to step 460. In step 460, hydrocarbons are dried on the surface without a particular pattern. The glass containing hydrocarbon chains is dried overnight at about 25° C. and placed into sterile nanopure water for no fewer than 2 hours.

After creating a particular pattern, step 450 transitions to step 470, hydrocarbons are dried on the pattern surface and printed onto optical-quality borosilicate glass. For masks, the glass with immobilized mask is treated with vacuum gas plasma. The glass containing hydrocarbon chains is dried overnight at 25° C. and placed into sterile nanopure water for no fewer than 2 hours.

To test the rates of cell fusion on the above described glass slides with a pattern surface, monocytes or macrophages are collected according to standard protocols and applied to hydrocarbon chain surface. After 30 minutes, the cultures are washed 3 times rapidly with phosphate-buffered saline to remove unbound cells, and complete cell culture medium (DMEM:F12, 10% FBS, 1% antibiotics) is applied to the culture for about 2 hours. After about 2 hours, about 10 ng/ml of interleukin-4 is applied to the culture to induce fusion and the culture is incubated until the respective time point.

Now referring to FIGS. 1A-lD, these figures illustrate macrophage fusion under a microscope. FIG. 1A illustrates that deposition of either isopropanol or toluene only on an optically clear glass slide by the method described promotes low levels of macrophage fusion. To the contrary, FIG. 1B illustrates that deposition of non-covalently coupled oleamide on an optically clear glass slide by the method described herein promotes high levels of macrophage fusion, as a result, multinucleated giant cells 110 are formed and can be visualized. Similarly, FIG. 1C illustrates that deposition of non-covalently coupled paraffin wax on an optically clear glass slide by the method described herein promotes high levels of macrophage fusion, as a result, multinucleated giant cells 120 are formed and can be visualized. Further, FIG. 1D illustrates that deposition of non-covalently coupled petrolatum on an optically clear glass slide by the method described herein promotes high levels of macrophage fusion, as a result, multinucleated giant cells 130 and 140 are formed and can be visualized.

Figure 2:
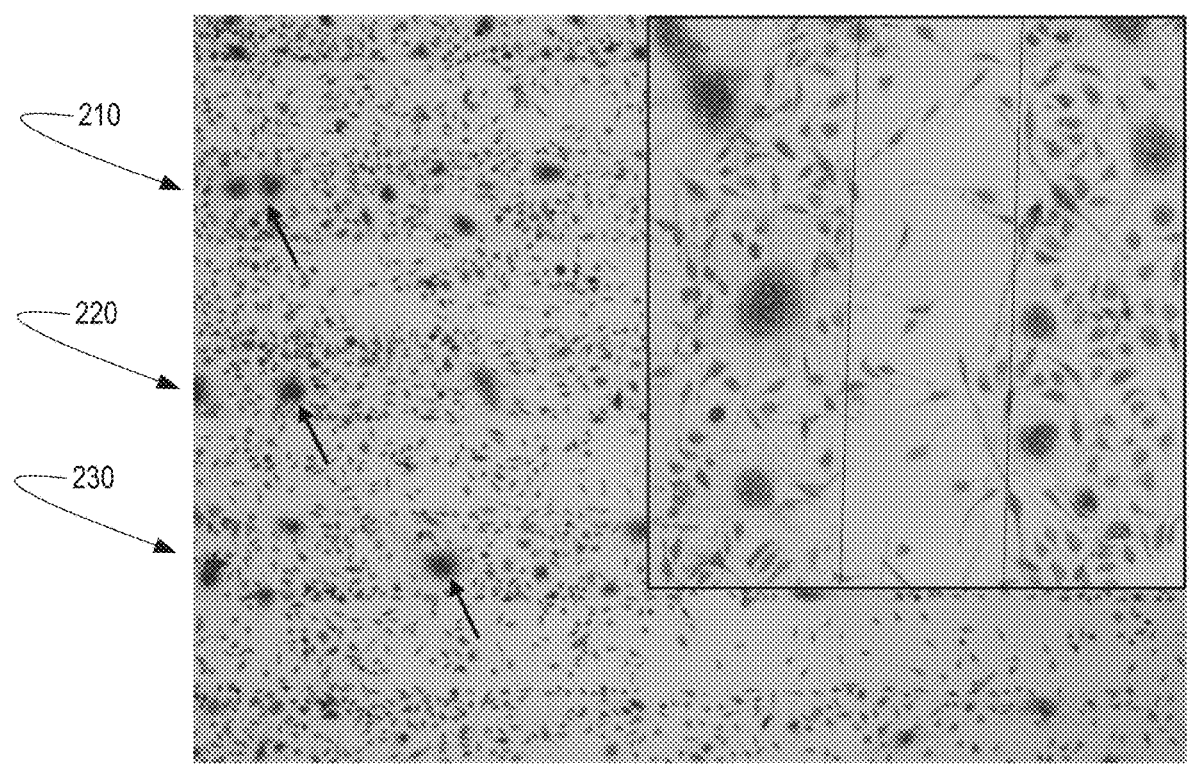
FIG. 2 illustrate that regions printed with hydrocarbon chains promote fusion. The low magnification view shows multinucleated cells in putative regions printed with hydrocarbon chains. The black arrows point to multinucleated cells. The high magnification inset more clearly shows the existence of multinucleated cells and regions in between print patterns devoid of fused cells.

FIG. 2 illustrates that patterns, i.e., defined regions promote high rates of cell fusion. Defined regions 210, 220, and 230 contain multinucleated giant cells.

Figures 3A, 3B:
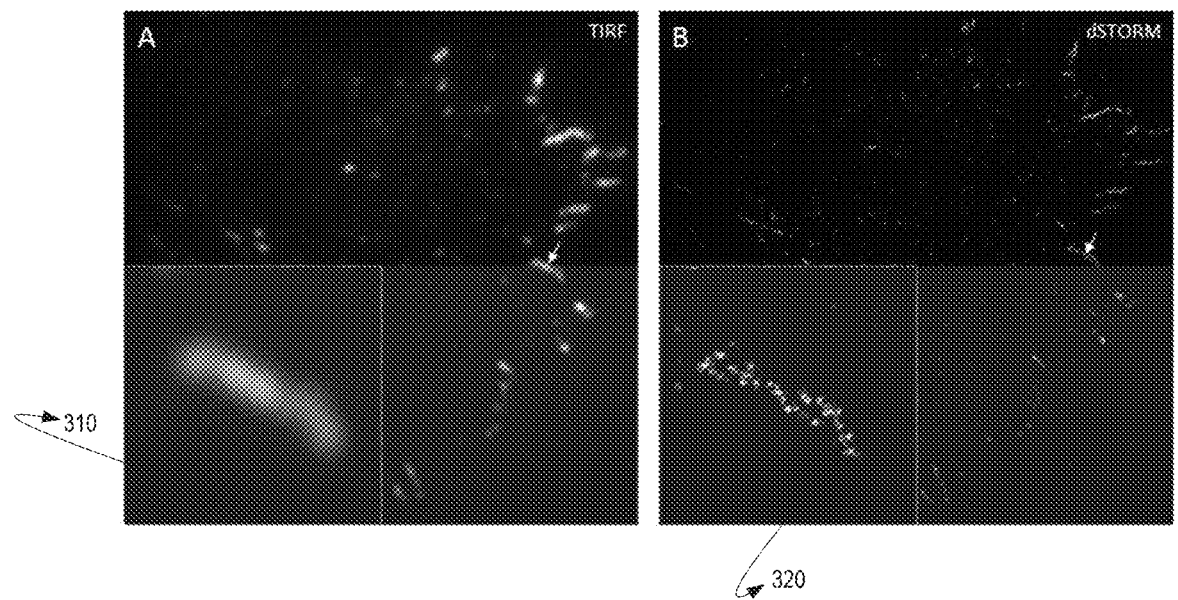
FIG. 3A is a glass surface adsorbed with hydrocarbon chains that are compatible with total internal reflection fluorescence microscopy. A total internal reflection image of a macrophage adhered to the chain-hydrocarbon surface. The inset at the bottom left corner shows a high magnification view of a focal adhesion (vinculin, white).
FIG. 3B is a direct stochastic optical reconstruction microscopy (dSTORM) super-resolution image of the same macrophage. The inset at the bottom left corner illustrates a dramatic improvement in resolution (vinculin, white). The white arrow points to the single focal adhesion that is shown in the inset in the lower left corner of the micrograph.

In certain embodiments, FIGS. 3A and 3B show that the optically clear glass surface with or without a pattern that promotes cell fusion formed by the method described herein is compatible with single-molecule super-resolution microscopy technologies. FIG. 3A shows a total internal reflection fluorescence (TIRF) microscopy image of formed MGCs on the glass surface. An inset 310 of FIG. 3A shows a high magnification view of a focal adhesion (vinculin is used to generate the contrast and other agent that is able to generate contrast can be used). FIG. 3B shows a direct stochastic optical reconstruction microscopy (dSTORM) super-resolution image of the same formed MGCs. An inset 320 of FIG. 3B demonstrates an improvement in resolution compared to inset 310.

Examples

Physical, Optical and Adhesive Properties of Paraffin-Adsorbed Surfaces

Figure 5A:
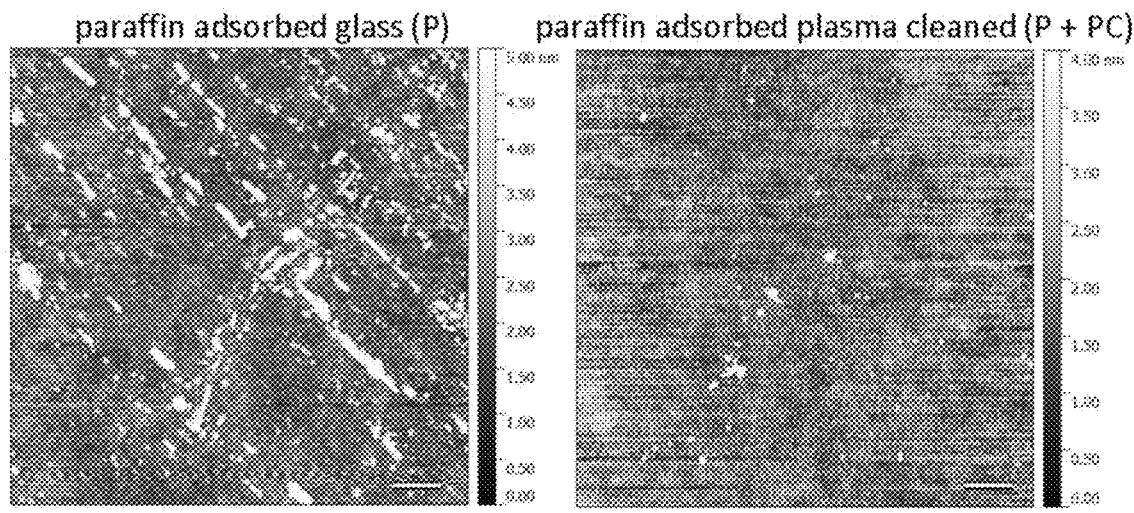
FIGS. 5A-5D illustrate characterization of surfaces adsorbed with paraffin. (A) AFM images of the nanotopography of paraffin-adsorbed and paraffin-adsorbed plasma cleaned surfaces. (B) Surface roughness as measured from 4-10 independent scans (10×10 µm). (C) Advancing water contact angle indicates that P surfaces are hydrophobic, whereas AC and P+PC surfaces are hydrophilic. (D) Representative intensity profiles for 100-nm TetraSpec beads on the AC, FD and P surfaces.
Figure 5B:
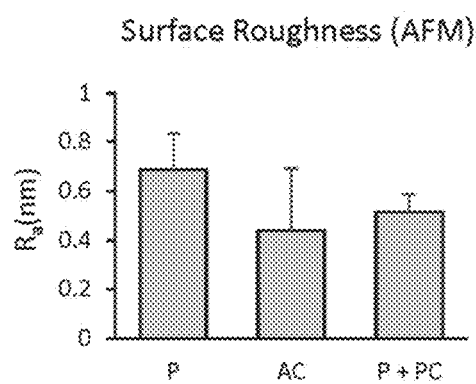
Figure 5C:
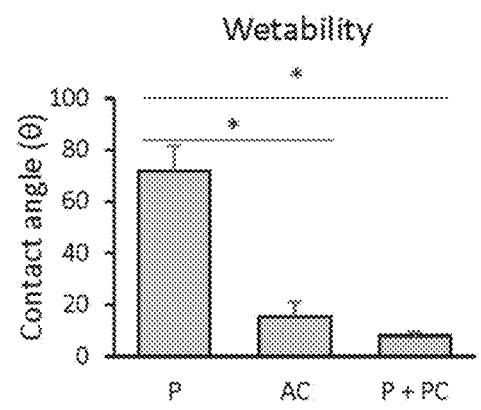

Having established that the surfaces adsorbed with hydrocarbon chain molecules exhibit high fusion-promoting capacity, we proceeded to investigate their physical, adhesive and optical properties. Since surfaces adsorbed with paraffin promoted the highest levels of macrophage fusion, we elected to utilize them to examine the surface topography, wettability and ability to support adhesion of Mac-1-HEK293 cells. Visualization of surface topography by AFM showed that paraffin-adsorbed glass (P surface) contained arrays of material that, at their peaks, were raised from the surface by 10 nm (FIGS. 5A and 5B). However, despite the presence of these arrays surface remained relatively flat (roughness 0.69±0.15 nm, FIGS. 5A and 5B). Treatment of the P surfaces with vacuum gas plasma (P+PC) removed most, but not all, of the paraffin (FIG. 5A) and slightly decreased surface roughness (0.52±0.07 nm; FIG. 5B). As determined by advancing water contact angle, adsorption of paraffin to AC glass strongly increased surface hydrophobicity of the P surface, while that of the P+PC surface remained low (FIG. 5C).

Figure 5D:
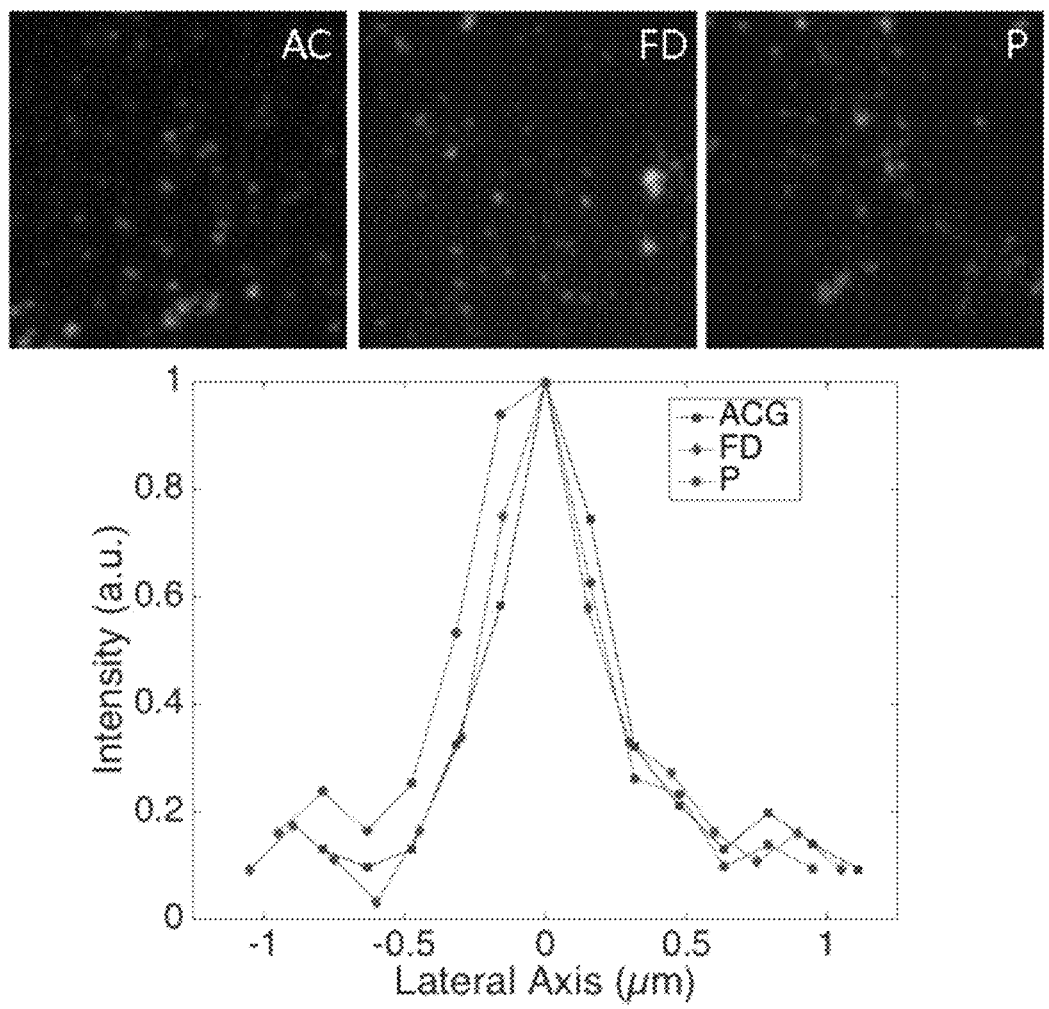

To examine how adsorption of paraffin influences the optical properties of the P surfaces, we imaged 100 nm Tetraspec beads (488 excitation) with total internal reflection fluorescence microscopy (TIRF). Qualitatively, the diameters of beads on the AC, FD and P surface did not appear to be different (FIG. 5D). Comparison of the lateral axis (i.e. bead diameters) showed that full width at half maximum obtained from Gaussian fits, which is a metric of optical resolution, was 305±28 nm, 313±23 nm, and 308±25 nm for AC glass, FD and P, respectively indicating that the surface should be amenable to most imaging techniques, including high resolution imaging.

Micropatterned Paraffin Imparts Spatiotemporal Control for MGC Formation

Figure 6A:
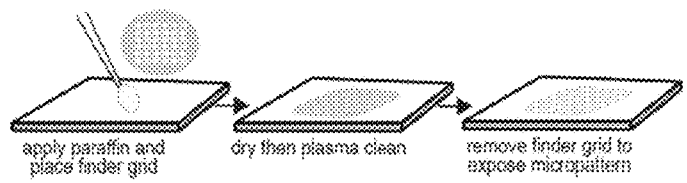
FIGS. 6A-6F show micropatterned P surfaces impart a high degree of spatiotemporal control over MGC formation. (A) Schematic of method used to create micropatterned paraffin prints on glass. Five microliters of a 1 mg/mL solution of paraffin in toluene is dispensed onto the glass surface and a finder grid is placed on the drop. After the solution dries the coverglass is plasma cleaned and only surface covered by the print remains fusogenic. (B) Phase-contrast micrographs show the formation of MGCs on the print. Time (hours:min:sec) is shown in the top right corner of each micrograph. Scale bars, 50 µm. In the final still frame, blue corresponds to Hoechst 33342, which labels nuclei. (C) Correlated light and scanning electron microscopy views on a micropatterned P surface show MGC formation form a mixture of eGFP- and mRFP-LifeAct cells. The scale bar corresponds to 25 µm. (D) The kinetics of fusion events on the micropatterned P and Permanox surfaces during 8 hr after the beginning of fusion (i.e. 9.5 hr after application of IL-4). Results shown are means±S.D. from three independent experiments. (E) Quantification of the types of fusion events during MGC formation on the micropatterned P and Permanox surfaces during 8 hours after the onset of fusion. The data are expressed as percent of the total number of fusion events detected on each surface and are means±S.D. from three experiments. (F) The kinetics of type 1, 2 and 3 fusion events on the micropatterned P surface during 8 hours after the onset of fusion at 9.5 hr. The data shown are means±S.D. from three experiments. A 20× field corresponds to 570×295 μm.
Figure 6B:
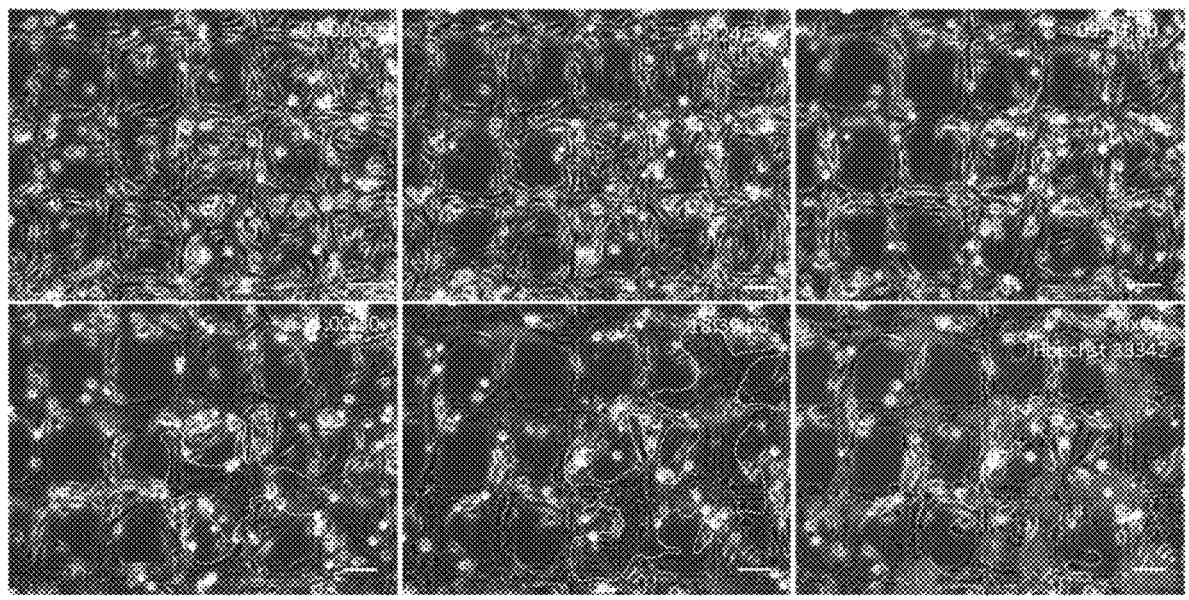
Figure 6C:
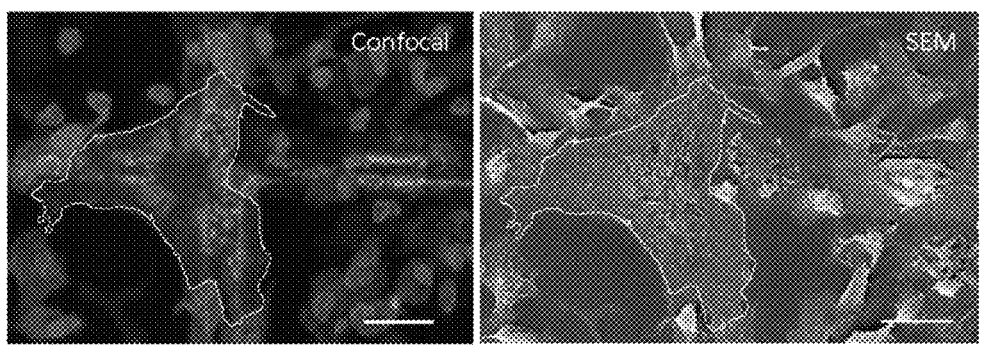

The P-surface enabled us to visualize sequential fusion events that led to the formation of MGCs. However, increasing magnification limits of the total observable area decreased the probability of observing macrophage fusion since it was still impossible to predict where fusion would eventually occur. Based on the previous report that used micropatterned substrates applied to plastic, we micropatterned paraffin in order to create defined fusogenic regions in a grid-like pattern (FIG. 6A). We observed not only the extraordinary rates of fusion (59±10%) corresponding to an additional 10% increase in the fusion index compared to the P surface, but a high degree of spatial control over the formation of MGCs (FIG. 6B). The MP grid system also enabled visualization of mixed populations of macrophages expressing eGFP- and mRFP-LifeAct with the ability to definitively show individual MGCs through SEM (FIG. 8C).

Figure 6D:
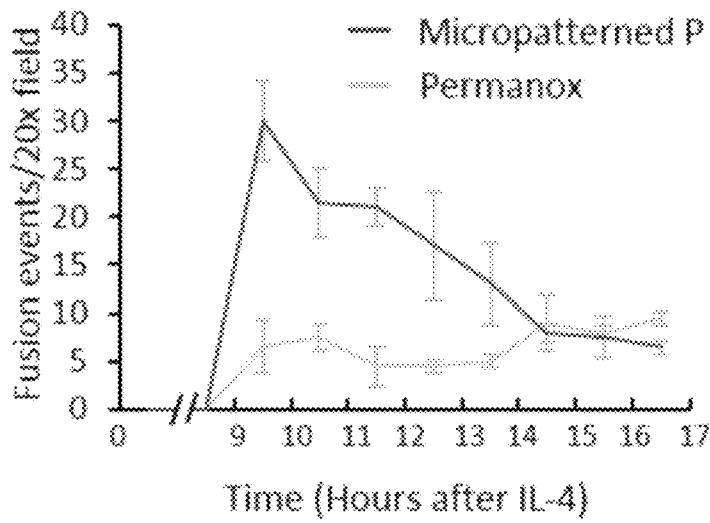
Figure 6E:
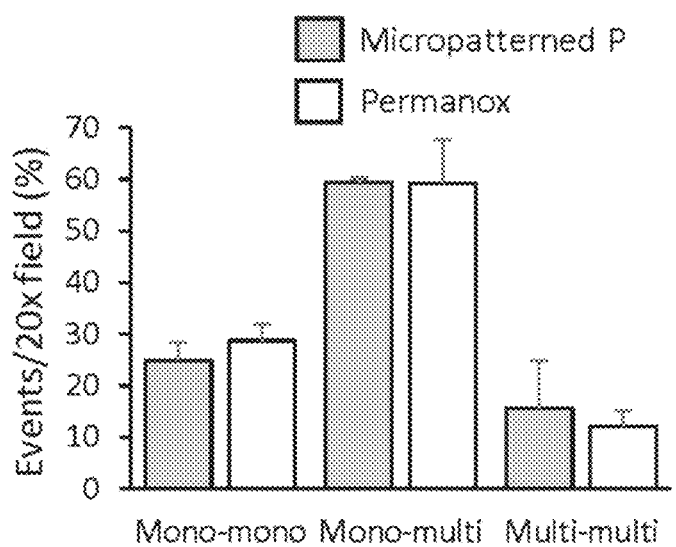
Figure 6F:
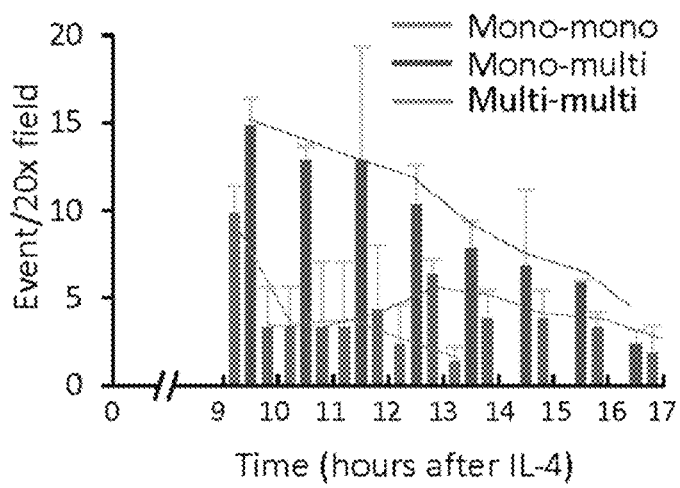

The use of the micropatterned paraffin (MP) surface enabled us to reveal the kinetics that govern the formation of MGCs (FIGS. 6D-F). Macrophage fusion began at 9.6±0.8 hr after the application of IL-4, at which time a sudden burst of fusion was observed. The number of fusion events per hour within the 8 hour imaging window gradually decreased over time (FIG. 6D). In total, we observed 125±22 (n=3) fusion events from the onset of fusion over the next 8 hr of observation when sampled with 20× objective magnification (570 μm×295 μm). At the end of this period, 71±17% of grid intersections contained MGCs. Since macrophage fusion and subsequent formation of MGCs have never been observed, we refer to mononucleated macrophages that undergo fusion with one another as founders. The formation of MGCs followed three distinct patterns. During the initial phase, fusion occurred between founders accounting for 25±3% of total events (FIG. 6E). We refer to these fusion events as type 1. Also, concomitant with type 1 fusion, mononucleated macrophages began to fuse with early multinucleated cells (type 2 fusion events) that accounted for 60±1% of total events observed. Fusion between MGCs (type 3 events) accounted for 15±9% of total events (FIG. 6E). While fusion between mononucleated macrophages ceased after the first 4 hours, fusion between mononucleated and multinucleated cells continued through the entire period of observation with the most robust fusion occurring during the first 4 hours (FIG. 6F). After which time, type 2 of fusion began to decline. Although rare, type 3 fusion events between two multinucleated cells were observed shortly after the initiation of the "fusion burst". The peak of type 3 fusion was observed at ~4 hour and then declined (FIG. 6F).

We next investigated whether the pattern of macrophage fusion on the MP surface, as evidenced by the type of fusion events, was comparable to that induced on Permanox™. Similar to the MP surface, fusion began 9.3±0.3 hr after the application of IL-4. However, we observed markedly fewer total fusion events (58±14, n=3; Supplemental video 3) during the next 8 hours. Nevertheless, the relative ratio of the types of events on Permanox was similar (FIG. 6E). In contrast to the MP surface, fusion on Permanox™ remained relatively constant over 8 hr observation period (FIG. 6F). Together, these data suggest that the MP and Permanox surfaces support similar types of fusion events; however, the MP surfaces promote more robust fusion.

Discussion

In this study we engineered an optical-quality glass surface that enabled us to observe in vitro macrophage fusion leading to the formation of MGCs. To our knowledge, no previous study utilized live imaging techniques to visualize directly the process of MGC formation. This deficiency is attributed mainly to two facts. First, the most commonly used surfaces that promote macrophage fusion are plastic (e.g. Permanox™, polysterene, etc.). However, some plastic is not amenable to most live imaging techniques. Second, optical-quality glass is required for microscopy, but it supports very low levels of macrophage fusion. The degree of fusion supported on optical-quality glass makes visualization of rare fusion events nearly insurmountable. We have overcome these limitations by engineering a glass surface that promotes high rates of macrophage fusion and at the same time enables the use of advanced live imaging techniques. We found that adsorption of oleamide, or other long hydrocarbon molecules, such as those present in paraffin or petrolatum, converted non-fusogenic glass into a fusogenic surface. Micropatterned glass surfaces further increased macrophage fusion and enabled a remarkable degree of spatiotemporal control over MGC formation.

The ability of oleamide to promote macrophage fusion has not been previous shown. We demonstrate that adsorption of oleamide onto clean glass increased fusion by ~4-fold. Similar to oleamide which contains 18 carbon atoms, long hydrocarbon molecules (20-40 C) present in paraffin and petrolatum were equally, if not more active. Characterization of the physical properties of the original FD and paraffin-adsorbed surfaces indicated that both surfaces are characterized by high hydrophobicity compared to clean glass (FIG. 5C). The requirement for hydrophobic surfaces to promote macrophage fusion has been reported in previous studies. It is also thought that the surface roughness affects macrophage fusion. Previous studies that investigated the effects of surface topology on macrophage fusion demonstrated that there was a 500 nm threshold for linear, parallel gratings of poly(ε-caprolactone), poly(lactic acid) and poly(dimethylsiloxane), below which macrophages did not fuse. Our AFM imaging data showed the existence of linear arrays of material on both the FD and paraffin-adsorbed surfaces (FIG. 5A). However, the calculated roughness indicated that the surfaces were rather flat and at the peaks, adsorbed material raised from the surface only by ~10 nm. Furthermore, there was no clear correlation between the surface roughness and fusion: while the roughness of the FD surface was ~2.5-fold higher than that of paraffin-adsorbed surface, the latter was significantly more active. These data suggest that although the surface roughness may be an important factor, the nature of adsorbed chemicals or the pattern of their deposition seems to be the key determinants of the fusion-promoting capacity of surfaces.

In adhesion assays, we found that on the FD and paraffin-adsorbed surfaces, integrin Mac-1 supported adhesion of Mac-1-HEK293 cells and mediated spreading of WT, but not Mac-1-deficient macrophages. Mac-1 is a multiligand receptor capable of binding numerous structurally and functionally unrelated molecules and is involved in numerous leukocyte responses, including adhesion, migration, phagocytosis and others. Recently, we and others demonstrated that Mac-1 is also essential for macrophage fusion on Permanox inasmuch as the ability of Mac-1-deficient macrophages to form MGCs was impaired. Furthermore, spreading of Mac-1-deficient macrophages on Permanox, but not adhesion per se, was strongly reduced. The latter observation is consistent with our data obtained with macrophages plated on the FD surface. The ability of Mac-1 to support adhesion via oleamide or other long hydrocarbon molecules adsorbed on glass suggests that Mac-1 may bind these molecules and thus directly link Mac-1-mediated recognition with fusion. How the engagement by Mac-1 of oleamide and other long hydrocarbon molecules transduce signals that influence the macrophage fusogenic state is under investigation.

The high fusion-promoting activity and preservation of optical qualities of paraffin-adsorbed glass (P) allowed us for the first time to conduct direct visualization of macrophage fusion and derive insights into the kinetics of the process. It should be noted though that while macrophage fusion on planar P surfaces is effective, this process is spatially stochastic that makes visualization of the MGC formation with high magnification optics a rather challenging procedure. Instead, the application of micropatterned paraffin allows for the precise localization of macrophage fusion to the predetermined spots and thus convenient point monitoring of the process. Notably, using this technique, we found that the process of fusion commenced ~9.5 hours after the application of IL-4, at which time a burst in fusion activity was observed. This finding suggests the requirement for a latent period during which a fusion-competent state in macrophages is apparently induced. Based upon the analyses of fusion that lasted 8 hours of continuous observation, we were able to distinguish three distinct types of fusion events that account for the formation of MGCs. Initially, fusion occurred between mononucleated macrophages (founder events, type 1) that was a prerequisite for the appearance of early multinucleated cells and the initiation of type 2 fusion between mononucleated and multinucleated cells (FIG. 6E). Type 2 fusions were by far the most predominant process during the MGC formation. Similar to type 1, type 3 fusion events were less frequent. It is interesting that macrophage fusion on Permanox, the most fusogenic plastic currently used in the field, was similar in the event type, but not magnitude, to that observed on micropatterned P glass. This indicates that the underlying mechanism responsible for MGC formation on both of these surfaces is similar and suggests that fusion of mononucleated with multinucleated cells is the predominant type of fusion. However, we cannot yet rule out the possibility that the fusion-promoting activity of Permanox may be attributed to oleamide, which is routinely used in plastic manufacturing. The fact that ~60% of plated macrophages participated in fusion on micropatterned P surface after 24 hours of culture indicates that they all acquired a fusion-competent state. The kinetics of fusion determined in the present study will be critical for the elucidation of key signaling, cytoskeletal and cell surface molecules involved in macrophage fusion.

Despite the long history of research on MGCs there have been no systematic studies to directly visualize fusion using living macrophages. Furthermore, no ultrastructural studies reported to date detected clear morphological changes that accompany fusion of macrophages that could have provided clues as to how two external plasma membranes fuse. As a consequence, unlike well-characterized phagocytosis mechanisms, the cellular and molecular mechanisms involved in macrophage fusion remain. Based on a limited number studies that utilized electron microscopy to study fusion, a model has been proposed that macrophage fusion may involve the phenomenon referred to as "cellocytosis". According to this idea, after the binding of one macrophage to the surface of another, it takes the lead and internalizes by sinking. During this process, the internalized cell is enveloped by two plasma membranes, one from the internalizer cell and one being its own plasma membrane. The two membranes then fuse and might be recycled to form the outer plasma membrane of MGC while the cytoplasm and organelles of both cells are integrated. Thus, the main feature of the proposed model is that two external membranes fuse after one cell has been internalized by other cell. In the present investigation, the fusion process appears to be phenotypically different than predicted by the "cellocytosis" model. Although we observed mononucleated macrophages shrouded by MGCs, out of >750 fusion events observed on the P and Permanox™ surfaces, we observed only two events that may fit a "cellocytosis" model. In these cases, fusion occurred from dorsal or ventral surfaces of the MGC. Rather, the intercellular interactions between the lateral margins with obvious phase-dark protrusions emanating between cells gave rise to fusion. Thus, direct visualization of macrophage fusion does not seems to support the "cellocytosis" model and suggests that the process involves other mechanisms. An alternative model might include the formation of a fusion pore between two cells, as proposed in other fusion systems. We have observed also macrophages actively migrating toward micropatterns. This observation, in conjunction with previous observations, supports the idea that macrophage migration is an important contributing factor to fusion. Future analyses of events occurring at the interface between live macrophages using the method described in the present study as well advanced live imaging techniques may reveal specific morphological features that govern fusion. This, in turn, may lead to a better understanding of the molecular mediators that govern the enigmatic macrophage fusion process.

Experimental Procedures

Mice

C57BL/6J and Mac-1-/- (B6.129S4-Itgamtm1Myd/J) mice were obtained from The Jackson Laboratory (Bar Harbor, Me.). LifeAct mice (Riedl et al., 2010) were a generous gift from Dr. Janice K. Burkhardt and used with permission from Dr. Roland Wedlich-Söldner. Mac-1-/- mice were housed in sterile cages. All mice were given ad libitum access to food and water and colonies were maintained at a constant temperature of 22° C. on a 12 hr light/dark cycle. All procedures were performed in accordance with the animal protocols approved by the Institutional Animal Care and Use Committee at the Arizona State University and the Mayo Clinic Arizona.

Macrophage Isolation and Cell Culture

Macrophages were isolated from the mouse peritoneum 72 hr after injection of a sterile 4% solution of Brewer's thioglycollate (Sigma Aldrich, St. Louis, Mo.). Mice were humanely sacrificed according protocols approved by both the Mayo Clinic, Arizona and ASU Animal Care and Use Committees. Immediately following euthanasia, 5 mL of an ice-cold solution of phosphate-buffered saline (PBS, pH 7.4) supplemented with 5 mM EDTA was injected aseptically into the peritoneum, the lavage containing cells was collected, and the cells were counted with a Neubauer hemocytometer. Low passage number (<10) HEK293 cells stably expressing human integrin Mac-1 and wild-type HEK293 cells were previously described (Lishko et al., 2003). The cells were cultured in the complete DMEM:F12 medium and detached from the culture dish by incubation in Cellstripper™ (Cellgro, Manassas, Va.). The cells were washed and then resuspended in the complete DMEM:F12 medium.

IL-4-Induced Macrophage Fusion

Peritoneal lavage cells were applied to various surfaces at a concentration of 2,000 cells/mm2 and incubated in 5% $CO_2$ at 37° C. for 30 min. Nonadherent cells were removed and adherent 18 macrophages were washed 3-5 times with Hank's Balanced Salt Solution (HBSS; Cellgro, Manassas, Va.) containing 0.1% bovine serum albumin (BSA) and allowed to incubate in the complete DMEM:F12 (Cellgro, Manassas, Va.) medium supplemented with 10% fetal bovine serum (FBS, Atlanta Biological, Atlanta, Ga.) and 100 I.U./mL penicillin, 100 µg/mL streptomycin (Cellgro, Manassas, Va.). After 2 hr, the medium was removed and fresh medium supplemented with 10 ng/mL of interleukin-4 (IL-4; Genscript, Piscataway, N.J.) was applied to the culture to induce fusion. In this study, the application of IL-4 is considered t=0. At the respective time points, cultures of fusing macrophages were washed 2 times with PBS and incubated with ice-cold methanol for 2 min. The fixed cultures were placed in an oven at 60° C. until dried. Wright's stain (Sigma Aldrich, St. Louis, Mo.) was applied for 8 minutes, the stain was removed and substituted with fresh buffered Wright's stain (pH 6.5) for an additional 8 minutes. The cover glass was placed under running deionized water to remove unbound stain and dried in an oven at 60° C. The cover glass was mounted in Permount™ (Thermo Fischer Scientific, Waltham, Mass.), the mountant was air dry, and the specimens were imaged with bright field optics. The extent of MGCs formation was evaluated by determining the fusion index. The fusion index is defined as the number of nuclei present in fused macrophages divided by the total number of nuclei in both fused and non-fused macrophages. Three to 5 bright field images collected at 20× objective magnification were analyzed per specimen.

Adhesion Assays

Cell adhesion was determined by plating 2.5×105 cells in 35 mm dishes (FluoroDish; World Precision Instruments, Sarasota, Fla.). Care was taken to ensure that cells spread evenly across the entire surface area of the dish for each experimental condition. After 25 min at 37° C. in 5% $CO_2$, cell images were captured before washing in order to standardize the number of cells in the field of view. Three phase contrast images (20× objective magnification) corresponding to the center of 19 the dish, the edge of the dish and the center-edge midpoint were collected for each sample. At 30 min, the specimens were washed gently 3 times with HBSS supplemented with 0.1% BSA and 3 images were collected as described above. Adhesion was calculated by dividing the average number of adherent cells after washing by the average number of total cells added before washing. For inhibition experiments, Mac-1-HEK293 cells were mixed with function blocking mAb 44a against the αM integrin subunit (10 µg/ml per $10^6$ cells) or an isotype IgG1 control for 15 min at 22° C.

Surface Characterization

Nanotopography of each surface was resolved using an atomic force microscope (AFM; Nanosurf, Woburn, Mass.). Scans (10×10 µm) were acquired in tapping mode with conical silicon AFM probes (Nanoscience, Phoenix, Ariz.). The nominal tip radius was 8 nm, and nominal resonant frequency was 300 kHz. Imaging was conducted in air at 22° C. Surface roughness was calculated using Gwyddion 2.45 software and represents an average of 3-5 randomly selected scans from at least 2 different preparations. Water contact angle was determined using an EasyDrop goniometer (Krüss, Matthews, N.C.). Water droplets (4 µL) were deposited on the sample surfaces, and their profiles were captured and analyzed for contact angle by the Drop Shape Analysis software (Krüss, Hamburg, Germany). 10 droplets were measured per each surface from at least 3 separate experiments.

Liquid Chromatography Mass Spectrometry

The composition of mixtures eluted from the FD dishes was determined by mass spectrometry. The LC/MS instrument consisted of a Dionex Ultimate 3000 Rapid Separation UPLC system equipped with a Dionex Ultimate 3000 autosampler and a Dionex Ultimate 3000 photodiode array detector coupled with a Bruker MicrOTOF-Q II quadrupole time-of-flight hybrid mass spectrometer using Hystar 3.2 software. The Bruker electrospray ionization source was operated 20 in the positive ion mode with the following parameters: end plate offset voltage=−500 V, capillary voltage=2000 V, and nitrogen as both a nebulizer (4 bar) and dry gas (7.0 L/min flow rate at 180° C. temperature). Mass spectra were accumulated over the mass range 50-3000 Da at an acquisition rate of 5,000 per second. Separations were performed on a Dionex Acclaim RSLC 120 C18 2.2 um 120 Å 2.1×100 mm column. The mobile phase (A=0.1% formic acid in water; B=0.1% formic acid in acetonitrile) gradient consisted of elution at 0.4 mL/min with 90% A/10% B for 2 min, followed by a 14-min linear gradient to 100% B, hold at 100% B for two minutes, then return to initial conditions for 2 minutes.

Single Cell Force Spectroscopy

Tipless silicon nitride cantilevers (HYDRA, AppNano, Santa Clara, Calif.) were prepared as described previously (Christenson et al., 2014). Briefly, cantilevers were plasma-cleaned at 29.6 W, 400 mTorr in O2 gas using a plasma cleaner (PDC-001, Harrick Plasma, Ithaca, N.Y.). Tips were functionalized by incubation in 2 mM (3-Aminopropyl) triethoxysilane (APTES, Sigma) in chloroform solution followed by changes of ethanol and then deionized water. Cantilevers were incubated in 1.25 mM Bis(sulfosuccinimidyl) suberate sodium salt (BS3, Sigma Aldrich, St. Louis, Mo.) solution for 30 min and then placed into 0.5 mg/ml concanavalin A (Sigma) solution for 30 min at 22° C. Cantilevers were then rinsed with PBS and stored in 1 M NaCl at 4° C. Functionalized cantilevers were used in a MFP-3D AFM (Asylum Research) placed on an inverted microscope (IX71, Olympus). Cantilevers were brought into contact with target cells manually, and withdrawn from the surface. Cells were allowed to firmly attach for 1 minute. SCFS measurements were conducted at 37° C. in HBSS with 0.1% BSA as described previously (Christenson et al., 2014). Force curves were recorded on different spots of the surface with a 2 nN trigger force and a 120 s dwell time. Approach and retraction speeds were 2 µm/s. Three-five force curves were generated for each cell and 6-12 cells were used for each condition.

Surface Fabrication

To prepare acid clean glass (AC), high stringency cover glass (Carolina Biological, Burlington, N.C.) was washed 3 times in hydrochloric acid, washed 10 times in copious volumes of nanopure water, washed 3 times in anhydrous acetone, washed an additional 10 times in nanopure water and stored in pure ethyl alcohol until use. Each washing step was 30 min and included either sonication or agitation. Plasma cleaned surfaces (PC) were prepared by exposure glass to vacuum gas plasma (Harricks, Ithaca, N.Y.) for 60 s. PC preparations were stored in a vacuum desiccator until use.

Oleamide (Sigma) was dissolved in isopropyl alcohol at a concentration of 1 mg/mL and used immediately thereafter. The solution was adsorbed to AC glass for 30 s, the excess solution was decanted, and the glass was allowed to air dry. DMSO-free paraffin wax (Sigma) and tocopherol-free petrolatum (Sigma) were solubilized in toluene at 1 mg/mL and 10 mg/mL, respectively. Cover glass was paraffinized by application of each solution for 30 s. Excess solution was removed and the surfaces were allowed to dry for a minimum of 12 hr. Prior to use, modified surfaces were polished by three strokes in x- and y-axis directions using a lint-free cloth. The surfaces were sterilized by UV irradiation for 15-30 minutes and washed aseptically with sterile water. In preliminary experiments, the lowest concentrations of paraffin, oleamide, and petrolatum that made AC glass fusogenic were determined.

Surface Micropatterning

In order to create a micropattern, a finder grid (Electron Microscopy Sciences, Hatfield, Pa.) was dipped in a 1 mg/mL solution of paraffin in toluene, excess liquid was removed with Whatman no. 1 filter paper, and the finder grid was placed in the center of the AC cover glass. The cover glass was allowed to air dry and then cleaned by vacuum gas plasma to remove paraffin between grid bars. The mask was carefully removed with Dumont no. 5 forceps (Electron Microscopy Sciences, Hatfield, Pa.) which left a pattern on the glass surface. Macrophage fusion was induced by IL-4 as described above.

Videomicroscopy

Micropatterned surfaces were fabricated as described above and affixed via cured PDMS to the bottom of a 35 mm culture dish whose center contained an 8 mm diameter void. Macrophages were applied to the glass and fusion was induced as described in the text above. The dish was transferred from the incubator to a stage-top incubation unit that was calibrated to consistently maintain a humified atmosphere of 5% CO2 in air at 37° C. Phase contrast images (20× objective magnification) were collected every 30 seconds with an Evos FL Auto (Thermo Scientific, Waltham, Mass.) and transferred to ImageJ to create videos.

Correlated Light Scanning Electron Microscopy (CLEM)

CLEM was conducted as previously described (Faust et al., 2014), albeit with minor modifications. Macrophages expressing eGFP- or mRFP-LifeAct were mixed in equal number and applied to paraffin micropatterned surfaces. Twelve hours after the application of IL-4 the specimens were fixed with 2% formaldehyde for 30 minutes. The specimens were washed 3 times for 10 minutes each and incubated with Hoechst 33342 as described by the manufacturer. Images were collected with a 20× (0.7 N.A.) objective via a Leica SP5 laser scanning confocal microscope and subsequently fixed with 2% glutaraldehyde prepared in 100 mM cacodylate buffer (pH 7.2). The specimens were washed with copious volumes of cacodylate and post-fixed with 1% OsO4 for 45 min. After washing with water, the specimens were dehydrated through a graded series of ethanol. The specimen was dried through the CO2 critical point and sputtered with Pt/Au. Images were collected on a JOEL JSM 6300 scanning electron microscope.

Direct Stochatic Optical Reconstruction Microscopy (dSTORM)

dSTORM was conducted as described previously. Fusing macrophages were detergent extracted with a solution containing 0.1% Triton X-100, 100 mM KCl, 5 mM MgCl2, 2 mM EGTA, 20 mM HEPES, pH 6.8 for 1 min at room temperature. Macrophages were fixed in 2% 23 formaldehyde made in 100 mM PBS (pH 7.2) for 15 min. The samples were washed 3 times for 15 min with PBS supplemented with 1% BSA (PBS-BSA) and incubated with a mouse anti-vinculin mAb (V9264, Sigma) at 4° C. overnight with gentle agitation. Antibody dilution buffer contains 100 mM KCl, 5 mM MgCl2, 2 mM EGTA, 0.01% Tween-20, 1% non-fat milk, 20 mM HEPES (pH 6.8). The specimens were washed 3 times for 15 min with PBS-BSA followed by an Alexa-657-conjugated secondary antibody (Thermo Fischer Scientific, Waltham, Mass.) at 4° C. overnight. The samples were washed with PBS and imaged immediately thereafter. Vectashield diluted in Tris-glycerol (Olivier et al., 2013), was used in combination with c.a. 12 mw laser excitation to achieve spatially separated single-molecule emitters. Emitters were collected in TIRF optics with a 100×1.4 N.A. objective and recorded with an Andor EMCCD operating in kinetic mode. Single-molecule localizations were reconstructed in RapidSTORM as described elsewhere (Wolter et al., 2012).

Statistics

Unless stated otherwise, results from three independent experiments are shown as mean±standard deviation (S.D.). Differences were determined by analysis of variance (ANOVA) followed by Tukey's or Dunn's post-test using GraphPad InStat software. Data were considered significantly different if post-tests indicated that $p<0.05$.

Although the embodiments are described in considerable detail with reference to certain methods and materials, one skilled in the art will appreciate that the disclosure herein can be practiced by other than the described embodiments, which have been presented for purposes of illustration and not of limitation. Therefore, the scope of the appended claims should not be limited to the description of the embodiments contained herein.

REFERENCES

All publications, including but not limited to patents and patent applications, cited below are herein incorporated by reference as though set forth in their entirety in the present application.

Riedl, J., Flynn, K. C., Raducanu, A., Gärtner, F., Beck, G., Bösl, M., Bradke, F., Massberg, S., Aszodi, A., Sixt, M. and Wedlich-Söldner, R., 2010. Lifeact mice for studying F-actin dynamics. *Nature methods,* 7(3), pp. 168-169.

Lishko, V. K., Yakubenko, V. P. and Ugarova, T. P., 2003. The interplay between integrins α M β 2 and α 5 β 1 during cell migration to fibronectin. *Experimental cell research,* 283(1), pp. 116-126.

Christenson, W., Yermolenko, I., Plochberger, B., Camacho-Alanis, F., Ros, A., Ugarova, T. P. and Ros, R., 2014. Combined single cell AFM manipulation and TIRFM for probing the molecular stability of multilayer fibrinogen matrices. *Ultramicroscopy,* 136, pp. 211-215.

Christenson, W., Yermolenko, I., Plochberger, B., Camacho-Alanis, F., Ros, A., Ugarova, T. P. and Ros, R., 2014. Combined single cell AFM manipulation and TIRFM for probing the molecular stability of multilayer fibrinogen matrices. *Ultramicroscopy,* 136, pp. 211-215.

Olivier, N., Keller, D., Rajan, V. S., Gönczy, P. and Manley, S., 2013. Simple buffers for 3D STORM microscopy. *Biomedical optics express,* 4(6), pp. 885-899.

Wolter, S., Löschberger, A., Holm, T., Aufmkolk, S., Dabauvalle, M. C., van de Linde, S. and Sauer, M., 2012. rapidSTORM: accurate, fast open-source software for localization.

What is claimed is:

1. An apparatus for visualizing cell fusion with a microscope, comprising a glass surface having a hydrocarbon coating, wherein the glass surface is configured to promote cell fusion and the hydrocarbon coating is non-covalently coupled to the glass surface, wherein the glass surface having a hydrocarbon coating further comprises a micropattern, wherein the micropattern comprises a grid pattern, and wherein the grid pattern comprises an array of hydrocarbon coating material raised from the glass surface to a peak of about 10 nm.

2. The apparatus of claim 1, wherein the hydrocarbon is selected from the group consisting of one or more of oleamide, paraffin wax, and petrolatum.

3. The apparatus of claim 1, wherein the glass surface is hydrophobic.

4. An apparatus for visualizing cell fusion with a microscope, comprising a glass surface having a hydrocarbon coating, wherein:
the glass surface is configured to promote cell fusion;
the glass surface further comprises a micropattern comprising a grid pattern; and
the hydrocarbon is selected from the group consisting of one or more of oleamide, paraffin wax, and petrolatum,
wherein the grid pattern comprises an array of hydrocarbon coating material raised from the glass surface to a peak of about 10 nm.

5. The apparatus of claim 4, wherein the glass surface is hydrophobic.

6. The apparatus of claim 1, wherein the grid pattern is treated with vacuum gas plasma.

7. The apparatus of claim 1, wherein the glass surface is treated with vacuum gas plasma.

8. The apparatus of claim 1, wherein the hydrocarbon coating further includes a monocyte or macrophage.

9. The apparatus of claim 8, wherein the monocyte or macrophage is treated with interleukin-4 or macrophage-1 antigen (Mac-1).

10. The apparatus of claim 1, wherein the glass surface is borosilicate glass with a thickness of about 0.10 mm to 0.25 mm.

11. The apparatus of claim 4, wherein the grid pattern is treated with vacuum gas plasma.

12. The apparatus of claim 4, wherein the glass surface is treated with vacuum gas plasma.

13. The apparatus of claim 4, wherein the hydrocarbon coating further includes a monocyte or macrophage.

14. The apparatus of claim 13, wherein the monocyte or macrophage is treated with interleukin-4 or macrophage-1 antigen (Mac-1).

15. The apparatus of claim 4, wherein the glass surface is borosilicate glass with a thickness of about 0.10 mm to 0.25 mm.

* * * * *